(12) United States Patent
Turner (10) Patent No.: US 10,512,716 B2
(45) Date of Patent: Dec. 24, 2019

(54) VENTILATION SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 306 days.

(21) Appl. No.: 15/532,639

(22) PCT Filed: Dec. 3, 2015

(86) PCT No.: PCT/GB2015/053694
§ 371 (c)(1),
(2) Date: Jun. 2, 2017

(87) PCT Pub. No.: WO2016/087859
PCT Pub. Date: Jun. 9, 2016

(65) Prior Publication Data
US 2017/0368247 A1    Dec. 28, 2017

(30) Foreign Application Priority Data

Dec. 3, 2014 (GB) .................................. 1421498.5

(51) Int. Cl.
*A61M 1/16* (2006.01)
*A61M 1/36* (2006.01)
(Continued)

(52) U.S. Cl.
CPC ............ *A61M 1/1698* (2013.01); *A61M 1/32* (2013.01); *A61M 1/3632* (2014.02);
(Continued)

(58) Field of Classification Search
CPC combination set(s) only.
See application file for complete search history.

(56) References Cited

U.S. PATENT DOCUMENTS 3,927,981 A    12/1975  Viannay et al.
4,493,692 A *   1/1985  Reed ..................... A61M 1/32
                                             128/DIG. 3
(Continued)

FOREIGN PATENT DOCUMENTS

GB    2 437 254    10/2007
GB    2 485 558     5/2012
(Continued)

OTHER PUBLICATIONS

United Kingdom Intellectual Property Office, Search Report under Section 17, Application No. GB1421498.5, dated May 18, 2015, 1 page.
(Continued)

*Primary Examiner* — Leslie R Deak
(74) *Attorney, Agent, or Firm* — Sunstein Kann Murphy & Timbers LLP (57) ABSTRACT

An oxygenation system for a ventilation system comprises an inlet for receiving oxygenation gas at an oxygenation gas flow rate into an oxygenator, and an exhaust gas remover to remove exhaust gas at an exhaust gas flow rate from the oxygenator, and one or more flow controllers for controlling the exhaust gas flow rate relative to the oxygenation gas flow rate. This allows the amount of total gas entering the oxygenator and the amount of total gas removed from the oxygenator to be controlled with greater accuracy.

15 Claims, 5 Drawing Sheets

(51) Int. Cl.
   *A61M 16/10* (2006.01)
   *A61M 1/32* (2006.01)
   *A61M 16/22* (2006.01)
(52) U.S. Cl.
   CPC ........ *A61M 1/3667* (2014.02); *A61M 16/101* (2014.02); *A61M 16/22* (2013.01); *A61M 2205/3334* (2013.01); *A61M 2205/3341* (2013.01)

(56) References Cited

U.S. PATENT DOCUMENTS

| | | | |
|---|---|---|---|
| 5,069,661 A | | 12/1991 | Trudell |
| 5,158,534 A | * | 10/1992 | Berry .................. A61M 1/1698 422/44 |
| 5,810,759 A | * | 9/1998 | Merz .................. A61M 1/1698 422/44 |
| 7,278,981 B2 | | 10/2007 | Ellingboe et al. |
| 8,585,968 B2 | | 11/2013 | Morley et al. |
| 2006/0144225 A1 | | 7/2006 | Downie et al. |
| 2010/0224192 A1 | | 9/2010 | Dixon et al. |

FOREIGN PATENT DOCUMENTS

| | | |
|---|---|---|
| WO | WO 03/092776 | 11/2003 |
| WO | WO 2015/047927 | 4/2015 |

OTHER PUBLICATIONS

Martin J. Amezaga, Authorized officer European Patent Office, International Search Report—Application No. PCT/GB2015/053694, dated May 13, 2016, 16 pages, together with the Written Opinion of the International Searching Authority.

* cited by examiner

VENTILATION SYSTEM

FIELD OF THE INVENTION

The present invention relates to a ventilation system. Particularly, the present system relates to a ventilation system for the oxygenation of blood and the removal of blood carbon dioxide. More particularly, the present invention relates to systems for and methods for improving automated ventilation and/or long-term ventilation to optimise patient care.

BACKGROUND OF THE INVENTION

Certain medical procedures require the heart or lung of a patient to be kept still. This may be necessary in order for a surgeon to perform surgical procedures, such as cardiac surgery. While the heart is unable to circulate blood or the lung is unable to re-oxygenate blood or to remove carbon dioxide, heart-lung machines are used for life support, providing extracorporeal oxygenation to maintain a supply of oxygen to a patient.

More recently, extracorporeal oxygenation has been explored for the management of viral infections (such as H1N1) that affect lung function by causing pulmonary embolisms. Patients suffering from such infections may require long-term ventilation, in the region of several weeks (typically 20 days, but in severe cases ventilation may be required for several months, e.g. for up to 180 days), in order to facilitate treatment and drainage of the lung, and in order to permit the lung to rest and heal while the patient's immune system is given an opportunity to defeat the viral infection.

The present invention seeks to improve ventilation management.

SUMMARY OF THE INVENTION

In accordance with a first aspect of the invention, there is provided an oxygenation system for a ventilation system as defined in claim 1.

The oxygenation system comprises an inlet for receiving oxygenation gas at an oxygenation gas flow rate into an oxygenator, and an exhaust gas remover to remove exhaust gas at an exhaust gas flow rate from the oxygenator. The oxygenation system further comprises one or more flow controllers for controlling the exhaust gas flow rate relative to the oxygenation gas flow rate.

A ventilation system is a system for extracorporeal oxygenation of blood, also known as a "heart-lung machine" or as an extra-corporeal membrane oxygenation (ECMO) system, which may be provided on a cart. A pump circulates the blood (heart function) and an oxygenator oxygenates the blood (lung function). Oxygen-depleted blood from a patient and oxygenation gas are received into the oxygenator. In the oxygenator, oxygen is taken up by the blood from the oxygenation gas, and carbon dioxide is released from the blood. The oxygenated blood is to be circulated back into the patient.

The oxygenation gas that is to be supplied into the oxygenator may have been blended (mixed) so as to have a predetermined composition of oxygen ($O_2$), nitrogen ($N_2$), and air (compressed air provided by hospital supplies). Traces of carbon dioxide and noble gases may be in the oxygenation gas.

In the oxygenator, blood haemoglobin releases carbon dioxide and may also release other gas such as waste anaesthetic gas. This gas is removed as exhaust gas through an oxygenator exhaust port.

Either the flow rate of the oxygenation gas into the oxygenator, or the flow rate of the exhaust gas out of the oxygenator, or both, may be adjusted by a flow controller. A flow controller may be provided for controlling the oxygenation gas flow rate. A flow controller may be provided for controlling the exhaust gas flow rate. The flow controller may be a high precision mass flow controller (MFC).

It will be understood that the oxygenation system may comprise means for determining the flow rate of one of the oxygenation gas or the flow rate of the exhaust gas, in order to determine by which amount the other of the flow rate of the respective other gas should be changed.

For instance, the oxygenation gas flow rate may be adjusted first, to ensure sufficient oxygenation gas entering the oxygenator to facilitate oxygen saturation of the blood. The oxygenation gas flow rate is then maintained at a suitable flow rate. The exhaust gas flow rate is adjusted relative to the oxygenation gas flow rate.

By being able to control the flow rate of the exhaust gas relative to the flow rate of the oxygenation gas, it is possible to determine with greater accuracy the amount of total gas entering the oxygenator and the amount of total gas removed from the oxygenator.

Also, this facilitates calculations that require a parameter related to the flow rate, and/or facilitates such calculations with greater accuracy. Such a parameter may be the actual flow rate of the oxygenation gas, the actual flow rate of the exhaust gas, and/or a difference between the gas flow rates.

In embodiments, the one or more flow controllers are configured to maintain a predetermined flow ratio of the exhaust gas flow rate to the oxygenation gas flow rate.

In embodiments, the one or more flow controllers are configured to maintain the exhaust gas flow rate at a predetermined offset level above or below the oxygenation gas flow rate.

By "maintaining" it is meant that the controllers are configured to be responsive to fluctuations in a gas flow rate. The gas flow rate may fluctuate for various reasons. For instance, the oxygenator may require a higher oxygen supply and a control unit may increase the supply of oxygenation gas by increasing the flow rate. A flow controller may be configured to adjust the exhaust gas flow rate in response to the increased oxygenation gas flow, so that the exhaust gas flow rate is set to a predetermined flow ratio or a predetermined offset.

Likewise, the exhaust gas flow rate may be determined by a hospital vacuum supply. The strength of the vacuum supply may vary. An exhaust gas flow controller may adjust the exhaust gas flow rate in response to a fluctuation to maintain a predetermined flow ratio or a predetermined offset.

As such, the oxygenation system may be regarded as a closed-loop control system that maintains the flow rates of the oxygenation gas and of the exhaust gas relative to the other.

This may also facilitate calculations, and/or improve the accuracy of calculations, by allowing simplifying assumptions to be made based on a defined flow rate ratio and/or on a defined relationship between the oxygenation gas and the exhaust gas. The controller may adjust the flow rate to a constant value. The controller may adjust the ratio to a constant value. In practice, the constant behaviour may be set for a limited period of time during which parameters for inclusion in a calculation are measured.

For instance, it may be possible to use sensors for determining the fraction of oxygen and/or carbon dioxide in a gas stream. From this, the amount of oxygen provided into the oxygenator and the amount of carbon dioxide withdrawn from the oxygenator can be determined, which, in turn, may provide an indication of the amount of oxygen taken up by the blood, and the metabolic activity of the patient. However, as the metabolic activity of a patient may change, the calculations can become complex if also a change of the gas flow rates has to be considered. Thus, the ability to make an assumption about the flow rates of the gas streams allows calculations to be carried out with greater accuracy.

Thus, if the flow rate of the oxygenation gas relative to the flow rate of the exhaust gas is maintained at a pre-determined ratio or at a predetermined offset, this facilitates the calculation of the uptake of oxygen by blood and of the release of carbon dioxide from the blood.

In embodiments, the one or more flow controllers are configured for maintaining the exhaust gas flow rate higher than the oxygenation gas flow rate.

Oxygenators are not air tight. Although connections at the supply side (the inlet for oxygenation gas into the oxygenator) are usually air tight, the outlet side typically comprises secondary outlets or safety valves that are provided for fail-safe purposes in the event that a primary outlet becomes blocked. A typical reason for a blockage is condensation. Due to the presence of secondary outlets, however, if exhaust gas is withdrawn from the oxygenator at a lower flow rate than the oxygenation gas supply, any excess oxygenation gas may pass from the oxygenator into the operating theatre (theatre=operation room) environment. Oxygenators are, therefore, also referred to as being porous.

If extracorporeal ventilation is used for a patient sedated by anaesthetic gas, e.g. during surgery, the anaesthetic may be circulated with the blood stream and may also be released by the blood inside the oxygenator. In that case, waste anaesthetic gas (WAG) may pass from the oxygenator, via one of its outlets, into the operating theatre. This may adversely affect clinical staff.

The ability to maintain the exhaust gas flow rate at a higher rate than the oxygenation gas rate allows ensuring that all oxygenation gas supplied into the oxygenator, as well as any gas released by the blood inside the oxygenator, is drawn out of the oxygenator and prevented from passing into the operating theatre.

In such scenarios, maintaining the exhaust gas flow rate at a predetermined ratio or at a predetermined offset above the oxygenation gas flow rate ensures that the waste anaesthetic gas removal continues in the event of gas flow fluctuations.

Being able to ensure that all exhaust gas is drawn away via an exhaust line is also beneficial if it is desired to relate the amount of carbon dioxide in the exhaust gas to the amount of carbon dioxide released by blood in the oxygenator.

In embodiments, the exhaust gas remover is vacuum-assisted to generate a vacuum-induced flow, to assist the removal of exhaust gas from the oxygenator. The flow generated over the oxygenator is, preferably, achieved at atmospheric pressure. In other words, there is no, or substantially no, pressure gradient across the oxygenator. However, preferably, the exhaust gas flow rate is larger than the oxygenation gas flow rate. This may also be referred to as flow gradient.

Using a vacuum-induced flow gradient allows the flow rate of the exhaust gas to be maintained at a higher level than the oxygenation gas flow rate even if the oxygenation gas is supplied at a low flow rate.

Furthermore, a flow gradient practically eliminates the risk of exhaust gas flowing back into the oxygenator and passing into the operating theatre.

In embodiments, the flow controller is configurable to maintain the flow rate of the exhaust gas removed from the oxygenator above a pre-determined threshold.

While the exhaust gas is withdrawn at a higher flow rate than the oxygenation gas supply, ambient air from the operating theatre may be drawn through any secondary outlets or valve configurations of the oxygenator into the exhaust gas stream. Particularly at low flow rates, exhaust gas has insignificant positive pressure to fully exit the exhaust port and leakage through the secondary exhaust ports is possible. In that case, it is difficult to relate the fraction of carbon dioxide in the exhaust gas to the carbon dioxide released by the blood, because the fraction of carbon dioxide can only be measured in a total volume comprising a volume of exhaust gas and an unknown volume of ambient air.

However, by maintaining the flow rate of the exhaust gas above a pre-determined threshold, a minimum gas flow rate and, thereby, a minimum flow rate out of the primary outlet of the oxygenator can be ensured. The minimum flow rate can be set to a level that ensures complete removal of the exhaust gas via the primary outlet.

If the fraction of ambient air drawn from the oxygenator with the exhaust gas is known, this allows an assumption to be made about the fractions of carbon dioxide in the exhaust gas originating from ambient air and the fraction released by the blood. For practical purposes, it can even be assumed that the carbon dioxide fraction in air is close to 0%, for the following reason. Carbon dioxide in air typically varies between 450 ppm and 600 ppm (ppm=parts per million). Typically, the fraction of carbon dioxide in the exhaust gas is between 1% and 10%, and so an error of 0.045 to 0.06% is negligible. However, the amount of ambient air drawn into the exhaust gas may vary considerably if the exhaust gas flow rate is not adjusted relative to the oxygenation gas flow rate.

Furthermore, knowledge of oxygen consumption and carbon dioxide production provides an empirical basis for optimising the composition of the oxygenation gas and for optimising the flow rates into and out of the oxygenator. This allows the composition and/or flow rate to be adjusted according to the development of a patient and helps automating the oxygenation of a patient. This is believed to be particularly useful for long-term extracorporeal ventilation.

In embodiments, the oxygenation system further comprises a processor and software instructions implemented by the processor, and the flow controller is controlled by processor.

In accordance with a second aspect of the invention, there is provided a blender for preparing an oxygenation gas in accordance with claim 9.

The blender comprises a first inlet for receiving gases into the blender, a blending unit for blending the gases into an oxygenation gas, a holding unit for storing the oxygenation gas after blending, an outlet to supply the oxygenation gas to an oxygenator; and a flow controller for controlling the flow rate of the oxygenation gas from the holding unit through the outlet.

Oxygenation gas is typically blended from gases supplied on site, e.g., from a hospital gas supply port, to provide a desired composition or ratio of oxygen in air in the oxygenation gas. This blending process is carried out in a blending unit of a blender. The hospital-supplied gases will be provided at a given flow rate, and it is difficult to reduce the gas flow from the hospital ports below a given minimum flow rate. Furthermore, in order to achieve required mix accuracy, it may be necessary to feed hospital-supplied gases into the blending unit at a minimum flow rate. For this reason, an oxygenation gas blended from hospital-supplied gases will, in the absence of a flow controller, leave the blender at a flow rate that is influenced by the minimum flow rate of the hospital-supplied gases.

A flow controller downstream of the blending unit allows the flow rate of the oxygenation gas to be adjusted to a flow rate that is lower than the sum of the flow rates of the gases blended into an oxygenation gas. More specifically, before passing through the flow controller, the oxygenation gas is buffered in a reservoir to facilitate blending. If, for any reason, more gas is blended than can be stored in the reservoir, gas that is not passed through the flow controller may be vented as excess gas into the atmosphere.

The flow controller allows the output flow rate of the oxygenation gas to be set at a flow rate outside the range achievable by the blending unit.

This allows the oxygenation gas to be provided at a low flow rate, while also ensuring that the components making up the oxygenation gas have been thoroughly mixed in the blender.

The oxygenation gas is supplied into an oxygenator of a ventilation system. A low flow rate facilitates a flow gradient out of the oxygenator if this is intended to be combined with an exhaust gas remover withdrawing exhaust gas at a higher flow rate than that of the oxygenation gas.

The embodiments of the second aspect are, therefore, directly related to embodiments of the first aspect. Embodiments of the first aspect and the second aspect may be combined. Such embodiments may be used to improve control of the flow gradient over an oxygenator in order to maintain a higher exhaust gas flow rate relative to the oxygenation gas flow rate, while also maintaining a low flow rate of the exhaust gas.

For instance, a flow-controlled blender may be combined with a vacuum-assisted exhaust line in order to optimise (a) the supply of oxygenation gas at low, constant flow rates at or near atmospheric pressure, (b) the withdrawal of exhaust gas at low, constant flow rates, and (c) the maintaining a sufficient flow gradient across the oxygenator at these low flow rates, or to optimise two of (a), (b), and (c).

In practice, the oxygenation gas may be supplied through the flow controller at a flow rate slightly above the required flow rate. The flow controller may be configured to bleed a marginal flow rate, e.g. in the region of 0.1 L/min, to fine-tune the required flow rate as required. However, there may be a minimum flow rate required to pass through the flow controller. For instance, it may not be possible to provide oxygenation gas below a flow rate of 1 L/min. In that case, the full difference to the required flow rate may be vented. E.g., if oxygenation gas is supplied to the flow controller at 1.0 L/min, but required at the oxygenator at only 0.6 L/min, the flow controller may vent 0.4 L/min.

Thus, oxygenation gas can be provided into the oxygenator within accurate flow rate margins despite being provided at low flow rates.

Embodiments may further comprise one or more sensors to measure one or more properties of the oxygenation gas indicative of its flow rate, composition, pressure, temperature, oxygen fraction, carbon dioxide fraction, or combination of two or more of these properties.

This allows properties of the oxygenation gas, after blending, to be determined. Counter measures can be taken if a property is not within predetermined parameters.

Also, these parameters may be used to improve the accuracy calculations to determine the amount of oxygen taken up by the blood or the amount of carbon dioxide released by the blood.

In embodiments, at least one sensor is configured to measure said property downstream of the flow controller.

In embodiments, at least one sensor is configured to measure said property upstream of the flow controller.

This allows properties of the oxygenation gas to be determined after the flow has been adjusted by the flow controller, or before this has been adjusted, respectively. If, for any reason, the flow rate or composition of the oxygenation gas is not within predetermined parameters, countermeasures may be taken.

In embodiments, the blender is configured to determine the difference between a property measured upstream of the flow controller and a corresponding property measured downstream of the flow controller, and to provide a signal if the difference exceeds a pre-determined threshold.

This provides a safety mechanism in case a property of the oxygenation gas is outside predetermined parameters. The signal may be in a form suitable for alerting a staff member. The signal may be an audible signal or a visual signal. The signal may be a machine-interpretable instruction to carry out a responsive action.

Embodiments may comprise a second inlet downstream of the flow controller and a bypass switch configured to receive gas from the second inlet.

Although the present invention contemplates blending the oxygenation gas and adjusting the flow so as to be able to provide oxygenation gas at a predetermined flow rate, it may be desirable to bypass the blending unit and the flow controller of the blender, e.g., for testing or maintenance purposes.

The gas for the second inlet may, for instance, be provided by a mechanical gas blender or by a flow-controlled emergency backup gas.

This also allows for failsafe operation in case of a system failure or power loss in either of the blending unit or the flow controller. By way of the failsafe mechanism, a continuous supply of oxygenation gas can be ensured.

In embodiments, the bypass switch is configured for activation to receive gas from the second inlet if the difference exceeds a pre-determined threshold.

If, after the oxygenation gas was prepared in the blending unit and its flow was adjusted by the flow controller, the parameters of the oxygenation gas are outside predetermined parameters, the bypass switch allows the supply of oxygenation gas to be switched to the second inlet.

In accordance with a third aspect of the invention, there is provided an oxygenation system for a ventilation system in accordance with claim 17.

The oxygenation system comprises an inlet for receiving oxygenation gas into an oxygenator and a low-pressure sub-system configured for connection to an external vacuum supply port. The low-pressure sub-system is configured to generate flow for removing exhaust gas from the oxygenator. The low-pressure sub-system is further configured for connection (a) to a venous drainage line and to generate a pressure gradient to assist blood removal via the venous drainage line, and/or to (b) to a hemo-concentrator and to generate a pressure gradient to assist the blood-concentrating by the hemo-concentrator.

Typically, an oxygenator comprises a reservoir into which blood from a patient is collected via a venous drainage line before being circulated to the oxygenator. This facilitates a continuous blood circulation through the oxygenator. Being able to apply a pressure gradient induced by a vacuum allows the drainage reservoir to be positioned at any height relative to the patient. However, hospital facilities may not always provide sufficient vacuum supply connectors. Retrofitting vacuum supply connectors may not be an available option. Thus, hospital facilities with a single vacuum supply may not be suitable for treatment requiring a plurality of vacuum supply connectors is required.

It is understood that by "vacuum" supply, a supply of low pressure suitable to generate a pressure gradient below standard atmospheric pressure is meant.

In such scenarios, if the available vacuum supply ports are required for critical systems, e.g. for waste anaesthetic gas removal, it may be necessary to ensure positioning of a venous drainage reservoir at a lower altitude than (i.e., below) a patient to ensure drainage. This impedes the manufacture of integrated systems.

Likewise, if every available vacuum supply port is used by a more critical system, it may not be possible to use a hemo-concentrator.

Providing a vacuum sub-system that generates a vacuum-induced flow for an oxygenator and a pressure gradient for venous drainage facilitates the integration of a venous drainage system. This reduces the reliance on multiple vacuum supply ports.

Providing a vacuum sub-system that generates a vacuum-induced flow for an oxygenator and a pressure gradient for blood concentration facilitates the integration of a hemo-concentrator. This reduces the reliance on multiple vacuum supply ports.

Embodiments of the third aspect may be combined with any of the embodiments of the first and second aspects, and combinations thereof.

This allows the vacuum usage to be better coordinated between multiple systems, e.g., by using a single hospital vacuum port to supply an exhaust gas removal line, a venous drainage line and/or a hemo-concentrator.

BRIEF DESCRIPTION OF THE FIGURES

Exemplary embodiments of the invention will now be described with reference to the Figures, in which.

DETAILED DESCRIPTION

Components Overview

Figure 1:
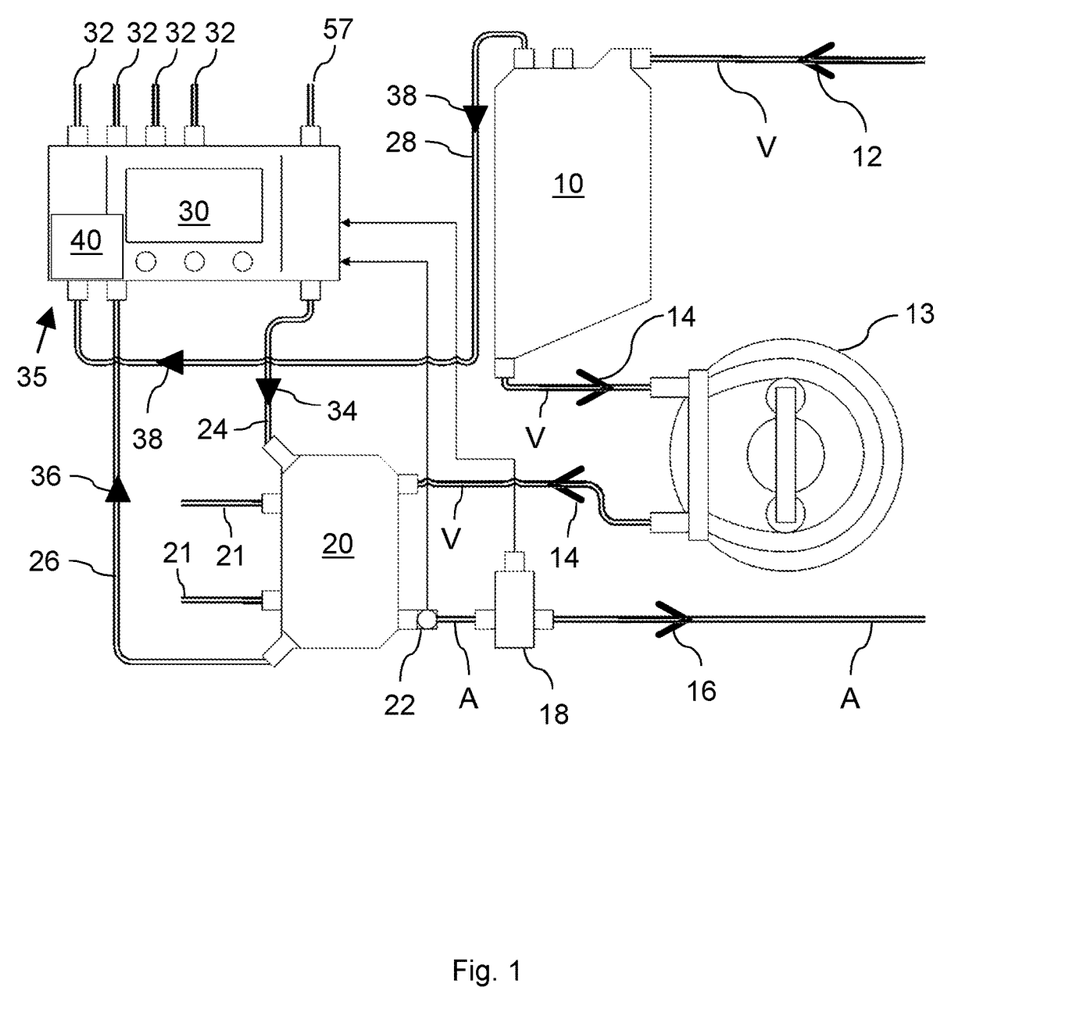
FIG. 1 shows a schematic layout of components of a ventilation system in accordance with an embodiment of the invention.

FIG. 1 provides an overview of system components of a ventilation system of the present invention. By way of background, an oxygenator is a device configured to receive oxygenation gas and venous blood, to re-oxygenate the blood by exposure to the oxygenation gas, and to provide oxygenated blood as arterial blood. Unused oxygenation gas is vented as exhaust gas which will also carry any gas given away by the blood. Put simply, a pulmonary (blood) bypass loop crosses a gas (oxygen) circulation loop. The pulmonary bypass loop circulates blood from a patient in order for the blood to be oxygenated and to be returned to the patient. The gas circulation loop provides the oxygenation gas for blood oxygenation.

Pulmonary Bypass Loop (Blood)

Venous blood from a patient (not shown in FIG. 1) is circulated in the direction indicated by arrow 12 towards a reservoir 10 via a venous line V. From the reservoir 10, the venous blood is pumped by a pump 13 in the direction indicated by arrows 14 towards an oxygenator 20. In the oxygenator 20, the blood is oxygenated. Blood leaves the oxygenator 20 to be supplied, as arterial blood, via an arterial line A in the direction indicated by arrow 16 towards a patient. A flow sensor 18 is provided to measure the flow rate of the re-oxygenated blood exiting the oxygenator 20. A temperature sensor 22 is provided to measure the temperature of the re-oxygenated blood exiting the oxygenator 20. Water lines 21 connect the oxygenator 20 to a water bath for maintaining a predefined temperature.

Oxygenation Gas Circulation/Supply Line

A gas circulator 35 comprises a blender 30 for preparation of oxygenation gases and a vacuum subsystem 40 for removal of exhaust gases.

Gases, such as nitrogen (N2) and oxygen (O2) of predetermined purity levels are supplied from hospital supply lines 32 into a gas mixer 52 of the blender 30. Compressed air with a composition of about 79% nitrogen and 21% oxygen may be supplied. Hospital-supplied gases may contain traces of carbon-dioxide and/or noble gases. The hospital mains also provide a source of low pressure or vacuum. The hospital supplies may also include oxygenation gas of a predetermined composition or oxygen at a predetermined purity level, which may be supplied via a supply line 57 to the blender 30.

In the blender 30, the gases are mixed to a composition that is to be supplied to the oxygenator 20 and fed in the direction indicated by arrow 34 via a supply line 24. In the oxygenator 20, the haemoglobin molecules of the venous blood are to take up oxygen and to release carbon dioxide. In the oxygenator 20, other gases, such as waste anaesthetic gases, may be released from or not be taken up in the oxygenator. Any gases released in or passing through the oxygenator 20 and gas components not taken up from the inlet gas are collected as waste gas or exhaust gas and leave the oxygenator 20 via an exhaust line 26 in the direction of arrow 36 and are transported away. The gas flow via the exhaust line 26 is assisted by a vacuum subsystem 40 that is part of the gas circulator 35.

Components Operation

The operation of the reservoir 10, the oxygenator 20, the blender 30 and the vacuum subsystem 40 will now be described in more detail with reference to FIGS. 2, 3, 4, 5, 6, 7 and 8.

Reservoir 10

Figure 2:
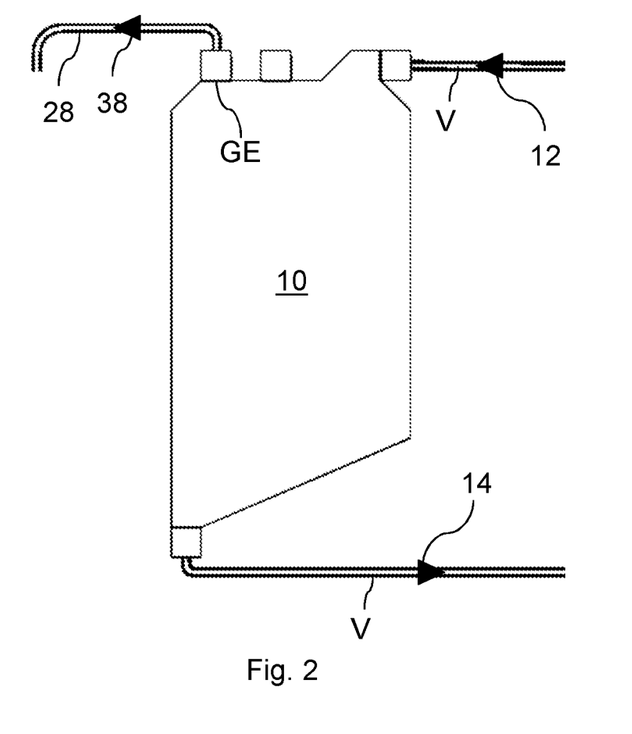
FIG. 2 shows a schematic illustration of a reservoir for use with a ventilation system in accordance with an embodiment of the invention.
Figure 3:
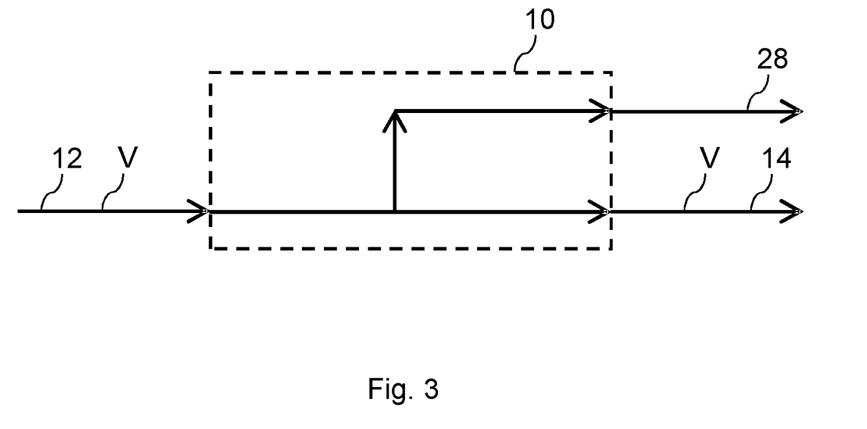
FIG. 3 shows a schematic flow analysis for the FIG. 2 reservoir.

Venous blood from a patient is collected in a cardiotomy reservoir (reservoir 10), shown in more detail in FIGS. 2 and 3. Blood drainage from a patient into the venous line V is improved by the vacuum-assisted venous drainage (VAVD) line 28. As indicated in FIG. 3, a pressure gradient 38 applied via the drainage pressure line 28 improves the drainage of blood via venous line V independent of the altitude of the reservoir 10 relative to a patient.

Oxygenator 20

Figure 4:
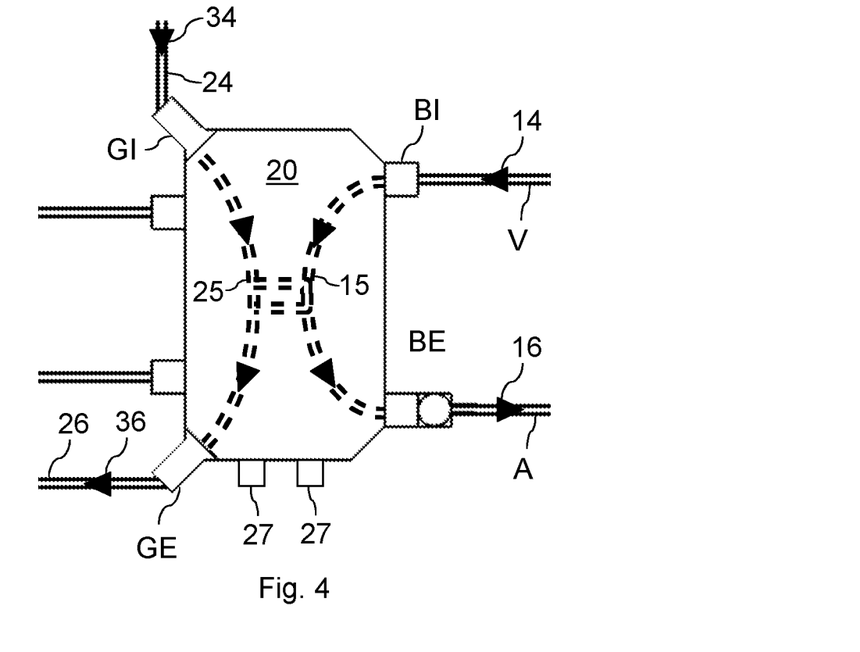
FIG. 4 shows an oxygenator of a ventilation system in accordance with an embodiment of the invention.
Figure 5:
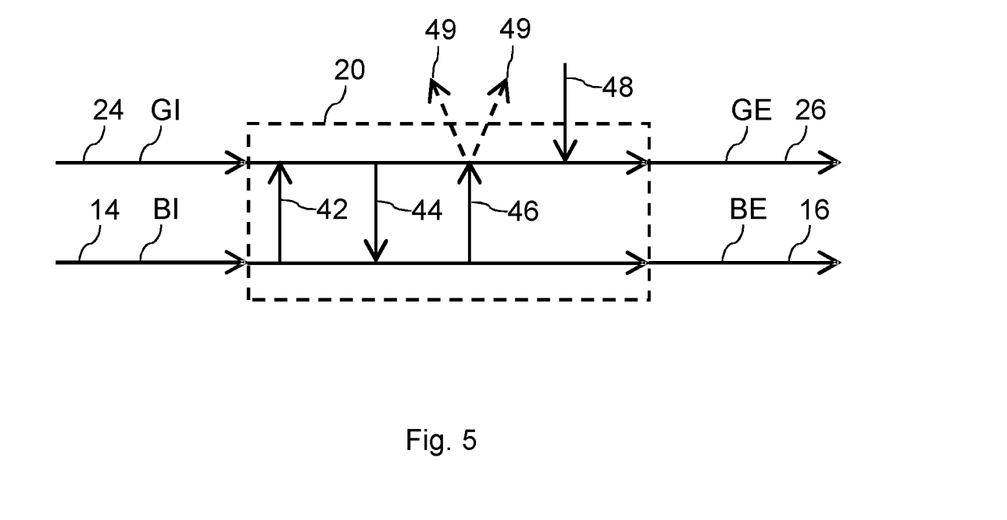
FIG. 5 shows a schematic flow analysis for the FIG. 4 ventilation system.

Venous blood carrying CO2 and waste anaesthetic gas (WAG) enters the oxygenator 20 via venous line V (in direction 14), as shown in detail in FIGS. 4 and 5. Venous blood enters the oxygenator 20 in a condition indicated herein by the symbol BI. In particular, the blood transports an amount of oxygen BIO2 and an amount of carbon dioxide BICO2 per unit of time.

FIG. 4 illustrates the uptake of oxygen by the blood in the oxygenator 20. The venous blood is transported within the oxygenator 20 along line 15 and exposed to the gas mixture, inlet gas GI from the blender 30, that is transported along the line 25. The gas mixture GI has a higher oxygen partial pressure and a lower carbon dioxide partial pressure than the haemoglobin in the blood, causing the haemoglobin to release CO2 and take up O2. Although FIG. 4 indicates, schematically, a concurrent exchange, oxygenators use, in practice, a countercurrent exchange.

FIG. 5 illustrates a flow diagram. In the oxygenator 20, CO2 is released from the blood into the gas stream, as indicated by arrow 42. The blood stream takes up O2 in a reaction indicated by arrow 44. Other components, such as waste anaesthetic gas, may not be taken up by the blood and enter or remain in the exhaust gas stream as indicated by arrow 46. Oxygenated blood is referred to as arterial blood. Blood is assumed to remain in the oxygenator for long enough to reach equilibrium oxygen saturation, so blood exiting the oxygenator via arterial line A in direction 16 is saturated with oxygen. I.e., the oxygen supplied with the oxygenation gas exceeded the oxygen-carrying capacity of the haemoglobin molecules in the blood.

The oxygenator 20 is not an air-tight unit. It may comprise one or more secondary exhaust ports 27 as a failsafe measure, to avoid pressure build-up within the oxygenator 20 if the exhaust line 26 is blocked. As or if a vacuum-induced flow is applied via exhaust line 26, this draws, therefore, not only exhaust gas GE from the oxygenator 20, but also ambient air 48 via secondary exhaust ports 27. To provide an illustrative example, for every 2 L of gas mixture supplied into the oxygenator 20 via supply line 24, 2.1 L of exhaust gas may be drawn through exhaust line 26.

The difference in flow rates that causes ambient air 48 to be drawn into the oxygenator 20 can also be used to ensure that any waste anaesthetic gas 46 is removed via the exhaust line 26. Thus, waste anaesthetic gas 46 is prevented from seeping out of the oxygenator 20, as indicated by arrows 49, into the operating theatre, where anaesthetic gases could affect staff.

Arterial blood leaves the oxygenator 20 in a condition BE. The amount of oxygen of the arterial blood BEO2 is related to the arterial oxygen saturation SaO2 and also depends on the haemoglobin concentration in the blood.

Exhaust gas GE which carries components released from the blood, such as CO2 from transfer 42 or waste anaesthetic gas that has not been taken up inside the oxygenator 20, is drawn via exhaust line 26 towards the vacuum sub-system 40 of gas circulator 35.

Blender 30

Figure 6:
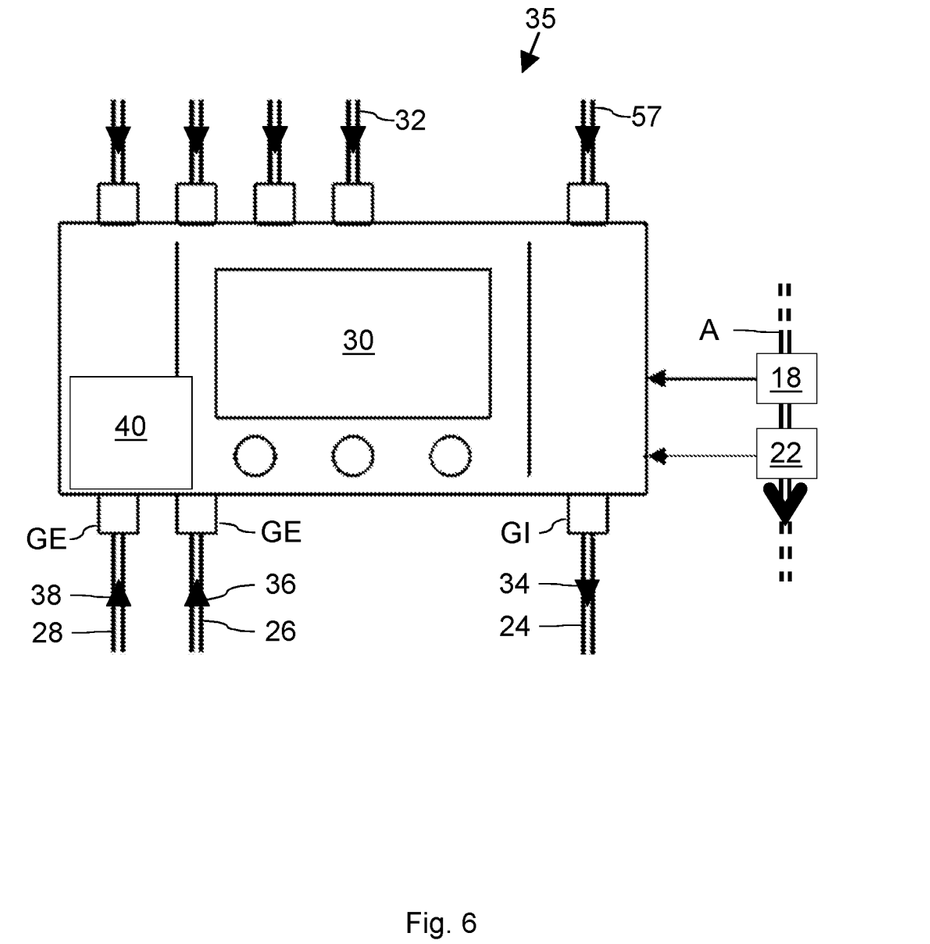
FIG. 6 shows a gas blender for use with a ventilation system in accordance with an embodiment of the invention.

In FIG. 6, the blender 30 is drawn enlarged as part of the gas circulator 35. Gas components supplied via inlets 32 are mixed to provide a supply gas for the oxygenator 20. The processing steps in the blender 30 are set out in FIG. 7. Hospital-supplied gases 32 are fed first into a gas mixer 52, and then passed through a flow control 54, a failsafe control 56, and sensors 58, before being supplied via supply line 24 to the oxygenator 20.

Gas Mixer 52

Figure 7:
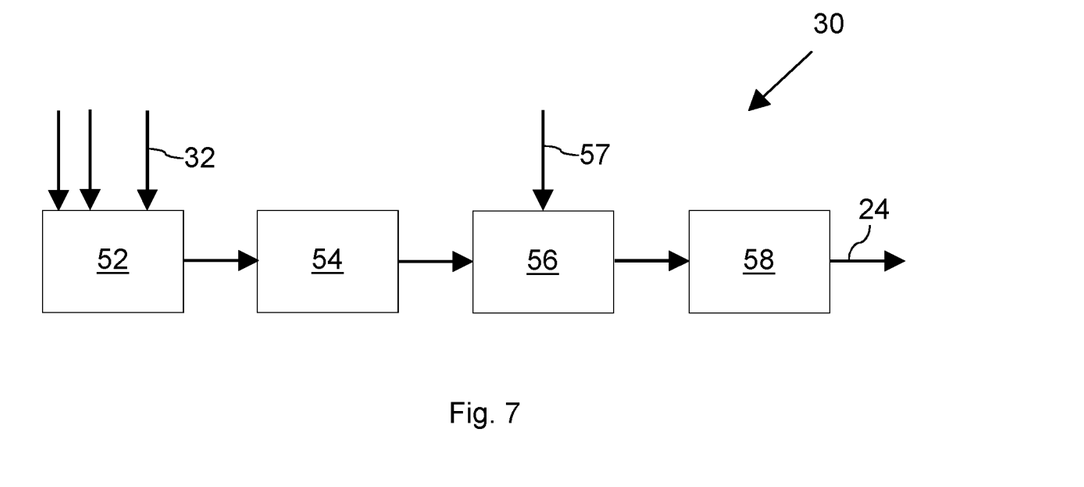
FIG. 7 shows a flow chart of the blender gas supply in accordance with an embodiment of the invention.

The gas mixer 52 comprises a mixing chamber into which component gases are received via an inlet and mixed to an oxygenation gas. The mixing chamber constitutes a blending unit in which the component gases are blended into an oxygenation gas. The mixing chamber also constitutes a holding unit or reservoir in which component gases may homogenise. The gas pressure may be controlled via a back pressure regulator. Excess gas may be vented into the atmosphere. From the mixing chamber of the gas mixer 52, the oxygenation gas passes through the blender flow control 54.

Blender Flow Control 54

The blender flow control 54 allows the flow rate of the gas mixture, the oxygenation gas, to be adjusted to a pre-determined flow rate. The blender flow control 54 controls the flow rate of the oxygenation gas from the holding unit, or mixing chamber, and thus constitutes a flow controller of the invention. This allows the amount of gas supplied to the oxygenator to be set, and allows this to be used in the calculation of oxygenation-related parameters.

A flow control unit in the blender allows the flow rate of the gas mixture to be set to low rates after it has been mixed as required. This improves the accuracy of the composition particularly at low flow rates, which are preferred in pulmonary systems.

It is difficult to achieve a good quality mixture of the oxygenation gas when throttling the flow rate of the hospital-supplied gas. Thus, to obtain an accurate mixture, the hospital-supplied gas is fed at a suitably high flow rate. The flow control therefore addresses the problem of how to obtain an accurately mixed oxygenation gas, while also providing the oxygenation gas to the oxygenator 20 at a low flow rate.

To illustrate this with an example, both oxygen and nitrogen may be supplied at 1.05 L/min. A 50%/50% mixture of these two gases would create a volume flow of 2.1 L/min (1.05 L/min+1.05 L/min=2.1 L/min). If, for instance, it is desired to supply only 2.0 L/min oxygenation gas to the oxygenator, the excess of 0.1 L/min (2.1 L/min−0.1 L/min=2.0 L/min) is vented, or "bled", into the atmosphere. Any suitable mixing ratios may be used in practice.

Failsafe Control 56

The failsafe control 56 provides an additional safety feature, by providing an option to switch to an external gas supply 57. In particular, the failsafe control 56 may be responsive to the gas mixer 52, the blender flow control 54, and/or sensors 58, and is configured to switch to the external gas supply 57 oxygen in the event one of the gas mixer 52 or the blender flow control 54 fail to provide oxygenation gas of pre-determined composition or flow rate.

The gas supplied via the external gas supply 57 may be pure oxygen. The gas supplied may be provided by a mechanical blender, or an emergency backup gas supply.

Sensors 58/Output Measurement

The sensors 58 are configured to measure parameters of the supply gas mixture. The parameters include the flow rate of the gas mixture, the pressure of the gas mixture, the temperature of the gas mixture, the oxygen concentration, the carbon dioxide concentration, or combinations thereof.

The values obtained by the output measurement can be checked against expected values and countermeasures can be taken in the event of any discrepancy. For instance, the flow rate as determined by sensors 58 can be compared to the flow rate set by the blender flow control 54. In the event of any discrepancy, countermeasures can be taken. Countermeasures include the generation of a notification signal, the increase or decrease of the flow rate by the blender flow control 54, or the switching to an external gas supply 57 by the failsafe control 56.

The sensors 58 allow the composition, pressure, temperature, and flow rate to be monitored regardless of the source, e.g., whether this is from gas mixer 52 or from an external gas supply 57.

The oxygenation gas of known properties leaves the blender 30 via an outlet to be supplied to the oxygenator 20.

Vacuum Subsystem 40

Figure 8:
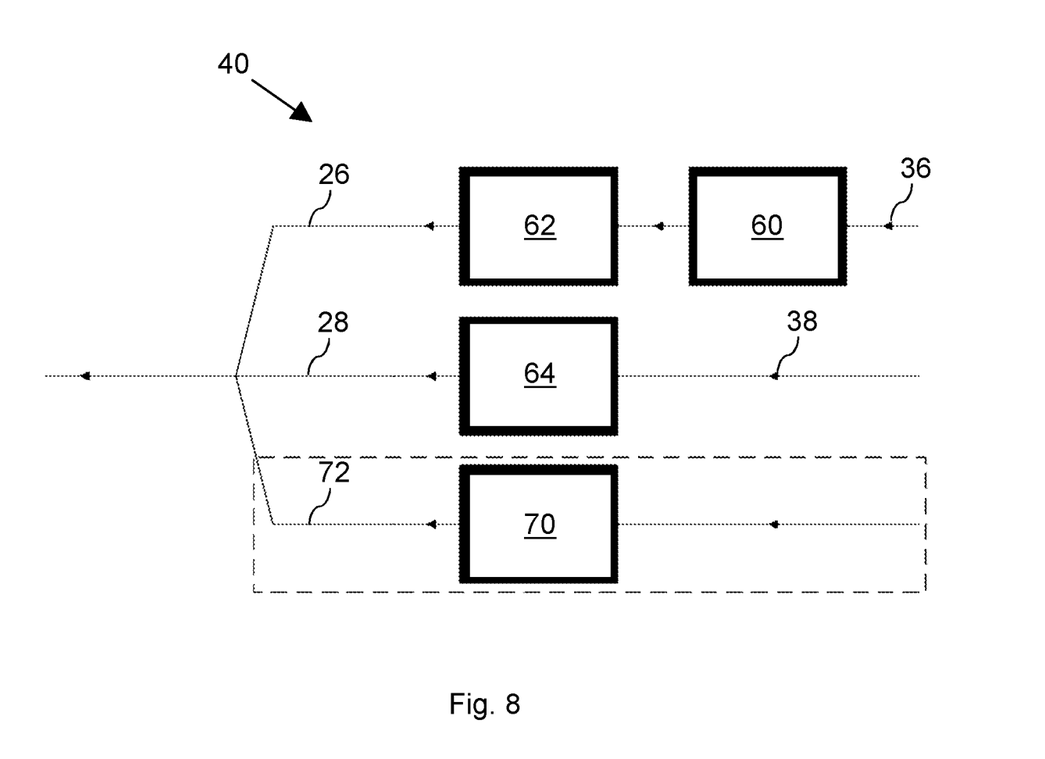
FIG. 8 shows a flow chart of the vacuum-assisted gas removal in accordance with an embodiment of the invention.

Vacuum may be used to create a flow gradient to assist gas flow. The vacuum pressure gradients are controlled by a vacuum subsystem 40 which in turn is supplied from a single vacuum supply, e.g. from a hospital.

The flow gradient in the exhaust line 26 is indicated by arrow 36 and pulls exhaust gas from the oxygenator 20 to the gas circulator 35. As indicated, the vacuum subsystem also generates and applies a pressure gradient in the direction indicated by arrow 38 in the drainage line 28 connecting the reservoir 10 to the gas circulator 35. The vacuum subsystem 40 may also provide a pressure gradient for the operation of a hemo-concentrator.

As illustrated in FIG. 8, the vacuum subsystem 40 comprises a WAG sensor 60 for the measurement of waste anaesthetic gas, and an exhaust flow control 62. The exhaust flow control 62 constitutes a flow controller of the invention and allows the flow of the exhaust gas GE drawn into exhaust line 36 to be determined or controlled. For example, this allows the amount of ambient air 48 that may be drawn into exhaust line 36 via oxygenator 20 to be modulated. Preferably, the flow rate of the exhaust gas relative to the flow rate of the oxygenation gas is controlled by one or both of the blender flow control 54 and the exhaust gas flow control 62.

To illustrate this with an example, supply gas GI may be supplied to the oxygenator 20 at a rate of 2 L/min. The rate of 2 L/min may be set in the blender 30 by flow control 54 and monitored by one of sensors 58. The exhaust flow control 62 may be set to a flow rate of 2.1 L/min. Thus, it can be assumed that, absent any influences by the blood oxygenation processes, 0.1 L/min (0.1 L/min=2.1 L/min exhaust gas−2.0 L/min inlet gas) of ambient air were drawn in via the oxygenator.

The vacuum subsystem 40 further comprises a vacuum pressure control 64 providing for the controlled depressurisation of the cardiotomy reservoir in order to improve the drainage of patient blood into the extracorporeal bypass.

Optionally, the vacuum subsystem 40 may generate a pressure gradient for use by a hemo-concentrator. The optional hemo-concentrator functionality is indicated in FIG. 8 by a dashed line. To this end, the vacuum sub-system comprises a vacuum pressure control 70 for a hemo-concentrator line 72. A hemo-concentrator is a device for extracting fluid from the blood, and is used, typically at the end of a surgical intervention, to remove excess fluid from the blood without removing wasting blood cells. This is achieved by a selectively permeable membrane between the blood and an outer chamber. The selectively permeable membrane is permeable for excess fluid but retains blood cells, and so the removal of fluid results in a relatively higher concentration of blood cells in the blood after removal of fluid. A vacuum-assisted pressure differential is applied via a hemo-concentrator line 72 creating a flow in the direction of to the outside in order to assist the removal of fluid.

All vacuum lines may comprise a mechanical pressure limit protection. This may be used to set a maximum positive (or upper) pressure close to atmospheric pressure. This may be used to set a maximum negative (or lower) pressure to prevent the building up of a pressure gradient across the oxygenator 20 in the event of a valve failure.

Pressure sensors may be provided to measure the pressure of the flow lines, the vacuum lines, and/or at vacuum connections. If a pressure value measured by one of these sensors is outside a predetermined threshold, e.g. outside a safe pressure range, a notification signal may be generated. For instance, the pressure of the hospital supply lines 32 and/or 57 may be monitored and the flow rates may be adjusted by blender flow control 54 and/or exhaust flow control 62, to maintain a predetermined flow rate or flow ration independent of any fluctuations.

Likewise, if the vacuum supplying the vacuum-assisted venous drainage fails, a notification signal may be generated that the drainage may need to be effected by other means than an assisted drainage, e.g., by positioning the reservoir below a patient.

The combination of the blender 30 and the vacuum sub-system 40 in a gas circulator 35 facilitates the integration of sensor and the evaluation of measured properties of the oxygenation gas and the exhaust gas (e.g., flow rate, pressure, temperature, composition, oxygen fraction, carbon dioxide fraction, and combinations thereof).

Furthermore, this facilitates taking into account certain maintenance functions. For instance, condensation may build up on a gas/blood membrane inside an oxygenator. In order to remove condensation, the gas flow of the oxygenation gas into the oxygenator may be moderately increased to blow out the condensation. The increased gas flow to blow out condensation is referred to as "sighing".

The gas circulator 35 may comprise, or be connected to, a controller that is configured to carry out a sighing procedure in regular intervals/at regular frequencies, or dependent on the flow rate. The parameters for sighing may be programmable into the controller.

Automating the sighing procedure by coordinating the oxygenation gas flow rate and the exhaust gas flow rate reduces the likelihood of condensation occurring and blocking the exhaust port of the oxygenator 20. This increases the period of time during which the oxygenation system may be operated without supervision.

The saturation of the arterial blood leaving the oxygenator 20 via line A may be measured by an oxygen sensor. Using calculations not specified herein, a determination can be made whether or not blood is fully (100%) saturated. During normal operation, the oxygenation gas flow rate is maintained to ensure 100% blood saturation.

However, over time, efficiency of an oxygenator may decline due to antibody (blood protein) build-up at the gas/blood membrane, clogging the gas/blood membrane and reducing the gas exchange capacity of the membrane. This may reduce blood oxygenation to below 100%. However, blood oxygenation may be reduced for other, e.g., medical, reasons. In order to determine whether a declining blood oxygenation is due to an oxygenator efficiency drop, the oxygenation gas flow rate may be temporarily and gradually reduced so as to reduce the blood oxygenation below the saturation value. Once this value has been determined, the oxygenation gas flow rate is increased to maintain full saturation.

The saturation value can be monitored over time. A decline in blood oxygenation may be indicative of an efficiency loss, and helps determining the oxygenator life span. This allows the replacement of oxygenators, or components such as its membrane, to be scheduled. Furthermore, if the efficiency loss occurs more rapidly than anticipated in view of comparable systems, this may be indicative of a catastrophic oxygenator failure. Thus, if a rapid efficiency loss is determined, a notification signal may be generated.

Although the gas supply 32 and 57 is described herein as being provided by a hospital, this is exemplary for a typical setting. The gas supply may be provided by another source. Any number and type of supply gases may be used, according to requirements.

The invention claimed is:

1. An oxygenation system for a ventilation system, the oxygenation system comprising
    an inlet for receiving oxygenation gas at an oxygenation gas flow rate into an oxygenator, and
    an exhaust gas remover to remove exhaust gas at an exhaust gas flow rate from the oxygenator,
    wherein the oxygenation system further comprises at least one flow controller for controlling the exhaust gas flow rate relative to the oxygenation gas flow rate, and
    wherein the at least one flow controller is programmed to maintain the exhaust gas flow rate higher than the oxygenation gas flow rate.

2. The oxygenation system according to claim 1, wherein the at least one flow controller is programmed to maintain a predetermined flow ratio of the exhaust gas flow rate to the oxygenation gas flow rate.

3. The oxygenation system according to claim 1, wherein the at least one controller is programmed to maintain the exhaust gas flow rate at a predetermined offset level above the oxygenation gas flow rate.

4. The oxygenation system according to claim 1, wherein the exhaust gas remover is vacuum-assisted to generate a vacuum-induced flow, to assist the removal of exhaust gas from the oxygenator.

5. The oxygenation system according to claim 1, wherein the flow controller is programmable to maintain the flow rate of the exhaust gas removed from the oxygenator above a pre-determined threshold.

6. The oxygenation system according to claim 1, further comprising a processor and software instructions implemented by the processor, and wherein the flow controller is controlled by a processor.

7. The oxygenation system according to claim 1, further comprising a low-pressure sub-system configured for connection to an external vacuum supply port; the low-pressure sub-system being configured to generate flow for removing the exhaust gas from the oxygenator; wherein the low-pressure sub-system is further configured for connection to at least one of:
    (a) a venous drainage line and to generate a pressure gradient to assist blood removal via the venous drainage, and
    (b) a hemo-concentrator and to generate a pressure gradient to assist the blood-concentrating by the hemo-concentrator.

8. The oxygenation system according to claim 1 further comprising a blender for preparing the oxygenation gas to be supplied to the oxygenator of a ventilation system, the blender comprising
    a first inlet for receiving gases into the blender,
    a blending unit for blending the gases to produce the oxygenation gas,
    a holding unit for storing the oxygenation gas after blending,
    an outlet to supply the oxygenation gas to an oxygenator, and
    a flow controller for controlling the flow rate of the oxygenation gas from the holding unit through the outlet.

9. The oxygenation system according to claim 8, wherein the blender further comprises at least one sensor to measure at least one property of the oxygenation gas indicative of at least one of its flow rate, composition, pressure, temperature, oxygen fraction, carbon dioxide fraction, and a combination of at least two of these properties.

10. The oxygenation system according to claim 9, further wherein the at least one sensor is configured to measure said property downstream of the flow controller.

11. The oxygenation system according to claim 9, wherein the at least one sensor is configured to measure said property upstream of the flow controller.

12. The oxygenation system according to claim 10, wherein the at least one sensor further includes a sensor configured to measure said property upstream of the flow controller.

13. The oxygenation system according to claim 12, configured to determine the difference between a property measured upstream of the flow controller and a corresponding property measured downstream of the flow controller, and to provide a signal if the difference exceeds a pre-determined threshold.

14. The oxygenation system according to claim 13, further comprising a second inlet downstream of the flow controller and a bypass switch configured to receive gas from the second inlet.

15. The oxygenation system according to claim 14, wherein the bypass switch is configured for activation to receive gas from the second inlet if said difference exceeds a pre-determined threshold.

* * * * *